(12) United States Patent
Bittenson

(10) Patent No.: US 10,143,827 B2
(45) Date of Patent: Dec. 4, 2018

(54) OPTOELECTRONIC SENSING OF A SUBCUTANEOUS IMPLANT SETTING

(71) Applicant: INTEGRA LIFESCIENCES SWITZERLAND SÀRL, Le Locle (CH)

(72) Inventor: Steven Bittenson, Bedford, MA (US)

(73) Assignee: INTEGRA LIFESCIENCES SWITZERLAND SÀRL, Le Locle (CH)

( * ) Notice: Subject to any disclaimer, the term of this patent is extended or adjusted under 35 U.S.C. 154(b) by 535 days.

(21) Appl. No.: 14/871,423

(22) Filed: Sep. 30, 2015

(65) Prior Publication Data
US 2016/0089519 A1 Mar. 31, 2016

Related U.S. Application Data

(60) Provisional application No. 62/057,688, filed on Sep. 30, 2014.

(51) Int. Cl.
*A61N 1/00* (2006.01)
*A61M 27/00* (2006.01)
*F16K 31/06* (2006.01)

(52) U.S. Cl.
CPC .......... *A61M 27/006* (2013.01); *F16K 31/06* (2013.01); *A61M 2205/04* (2013.01); *A61M 2205/3334* (2013.01); *A61M 2205/50* (2013.01); *A61M 2205/502* (2013.01); *A61M 2205/587* (2013.01)

(58) Field of Classification Search
CPC ...... A61M 2205/04; A61M 2205/3334; A61M 2205/50; A61M 2205/502; A61M 2205/587; A61M 27/006; F16K 31/06
See application file for complete search history.

(56) References Cited

U.S. PATENT DOCUMENTS

| | | |
|---|---|---|
| 7,191,011 B2 | 3/2007 | Cantlon |
| 7,844,342 B2 | 11/2010 | Dlugos, Jr. |
| 7,899,544 B2 | 3/2011 | Cantlon |
| 8,357,145 B2 | 1/2013 | Schleicher |
| 8,630,695 B2 | 1/2014 | Negre |
| 8,784,332 B2 | 7/2014 | Wolf, II |
| 8,961,448 B2 | 2/2015 | Forsell |
| 2004/0055610 A1 | 3/2004 | Forsell |
| 2004/0064030 A1 | 4/2004 | Forsell |
| 2004/0098113 A1 | 5/2004 | Forsell |
| 2004/0250820 A1 | 12/2004 | Forsell |
| 2006/0124140 A1 | 6/2006 | Forsell |
| 2007/0005071 A1 | 1/2007 | Kucklick |
| 2007/0078391 A1 | 4/2007 | Wortley |
| 2009/0105688 A1 | 4/2009 | McIntyre |
| 2012/0046536 A1 | 2/2012 | Cheung |
| 2012/0083856 A1 | 4/2012 | Thacker |
| 2012/0316486 A1 | 12/2012 | Cheung |
| 2014/0052047 A1 | 2/2014 | Wilson |

(Continued)

FOREIGN PATENT DOCUMENTS

| | | |
|---|---|---|
| EP | 2526994 A1 | 11/2012 |
| EP | 2777751 A2 | 9/2014 |

*Primary Examiner* — George Manuel
(74) *Attorney, Agent, or Firm* — Troutman Sanders LLP

(57) ABSTRACT

Systems and methods are provided for optically reading a setting of an implantable valve. The valve includes optical emitters that are wirelessly powered by a valve reading tool that images the emitted light to determine the valve setting.

22 Claims, 2 Drawing Sheets

(56) References Cited

U.S. PATENT DOCUMENTS

| | | | |
|---|---|---|---|
| 2014/0054883 A1* | 2/2014 | Lanigan | A61M 39/1011 285/33 |
| 2014/0135597 A1 | 5/2014 | Wolf, II | |
| 2014/0135647 A1 | 5/2014 | Wolf, II | |
| 2014/0243703 A1 | 8/2014 | Schmidt | |
| 2014/0257166 A9 | 9/2014 | Wolf, II | |
| 2015/0182734 A1 | 7/2015 | Miethke | |

* cited by examiner

OPTOELECTRONIC SENSING OF A SUBCUTANEOUS IMPLANT SETTING

FIELD OF THE INVENTION

The present inventions relates generally to extracorporeal tools and methods for locating and reading a setting of a surgically implantable device and specifically to optoelectronic tools and methods for reading a setting of an adjustable implantable valve.

BACKGROUND OF THE INVENTION

Surgically implantable pumps or valves are used to treat various medical conditions that require long-term delivery of therapeutic drugs such as pain medication, or that require drainage of abnormal fluid accumulation in disorders such as hydrocephalus, a neurological condition in which drainage of cerebrospinal fluid (CSF) from the ventricles, or cavities, of the brain, is blocked in some way. Blockage of this drainage increases pressure on the brain that, left untreated, can result in serious medical conditions including subdural hematoma, compression of the brain tissue, and impaired blood flow.

Hydrocephalus is most often treated by surgically inserting a CSF drainage device, typically called a shunt, to controllably drain excess fluid from a ventricle to another area of the body where it can be absorbed or eliminated. Often the shunt system includes a valve that is noninvasively adjustable through the patient's skin so that a medical practitioner can provide a flow or pressure settings that are appropriate for a patient's condition over time.

It is important for medical practitioners to be able to accurately identify the location of an implanted valve under the patient's skin, to read a setting of the valve, and to adjust the valve's setting. The implanted valve is typically palpatable through the patient's skin and many tools for locating the valve are shaped to complement a physical profile of the valve so that the tool can be positioned and oriented correctly on the patient's skin over the valve, and then held in place for reading and setting the valve using one or more additional tool. Proper positioning of such physical locator tools depends on the valve being reliably palpatable through overlying skin, a characteristic that can be compromised by swelling of tissue near the valve, or by other variations from patient to patient. In addition, application of a conformal locator tool can also be a cause of patient discomfort.

Often, separate tools and complex, time-consuming operational steps are required to perform the locating, reading and setting functions noninvasively. Some types of valves are read using x-ray imaging. Some other valves include a magnetic rotor, an orientation of which can be read using a magnetic compass-like device or one or more magnetic field sensors physically registered to a locator device. Many valves are adjusted using strong magnets applied from outside the body. Commonly, the presence of a strong adjusting magnet prevents the user from reading the valve while setting it.

Accordingly, a need exists for improved tools that enable noninvasively adjustable implanted valves to be located, read and adjusted simply and reliably.

SUMMARY

Apparatus, systems and methods are disclosed incorporating implantable valves, settings of which can be read optically. One aspect of the present invention is a valve for implantation beneath the skin of a patient. The valve includes a fluid inlet port, a fluid outlet port and a restriction element for restricting fluid transport between the inlet port and the outlet port. A control member is coupled to the restriction element for setting at least one of a rate of fluid flow through the restriction element and a pressure drop across the restriction element. A physical orientation of the control member indicates the setting of the valve. At least one light-emitting element is coupled to the control member, wherein light emitted by the light-emitting element is externally detectable through the skin of the patient for reading the valve setting. The valve can include a housing that transmits the emitted light.

Two spaced-apart light emitters can also be positioned on the control member and the two light-emitting members can have different emission wavelengths or different pulse frequencies of the light emission. The light emitters can be light-emitting diodes and can have emission wavelengths in the visible or near infrared spectral region. The emitted light is preferably detectable through the skin of the patient. The valve can also include one or more additional light-emitting elements that are not mounted on or to the control member. Further, the valve can include an antenna for receiving an externally generated electromagnetic signal and for providing electrical power to the light-emitting elements.

Another aspect of the invention is a method for noninvasively reading a setting of an adjustable valve implanted beneath the skin of a patient. The method comprises detecting through the skin, light emitted by at least three physically distributed light sources within the valve. The method further includes mapping the relative locations of the at least three light sources, and calculating a current setting of the valve from the mapped locations.

Yet another aspect of the present invention is a system for reading a setting of an adjustable fluid flow valve implanted beneath the skin of a patient. The system includes an electronic imaging array for imaging light emitted by at least three light emitters on the valve and transmitted through the skin. The system also includes an electronic processor for determining the setting of the valve from the image, and a display for indicating the setting of the valve.

The imaging array can be positioned on or near the skin of the patient above the implanted valve to read the valve. The display can be used to present information associated with one or more of a location, an orientation and a setting of the valve.

The valve can be a magnetically adjustable valve, and the system for reading the valve can further include a magnetic tool component for adjusting a setting of the valve. The imaging array can be planar and positionable between the magnetic tool component and the skin above the valve.

BRIEF DESCRIPTION OF THE DRAWINGS

This invention is described with particularity in the appended claims. The above and further aspects of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DESCRIPTION

Figure 1:
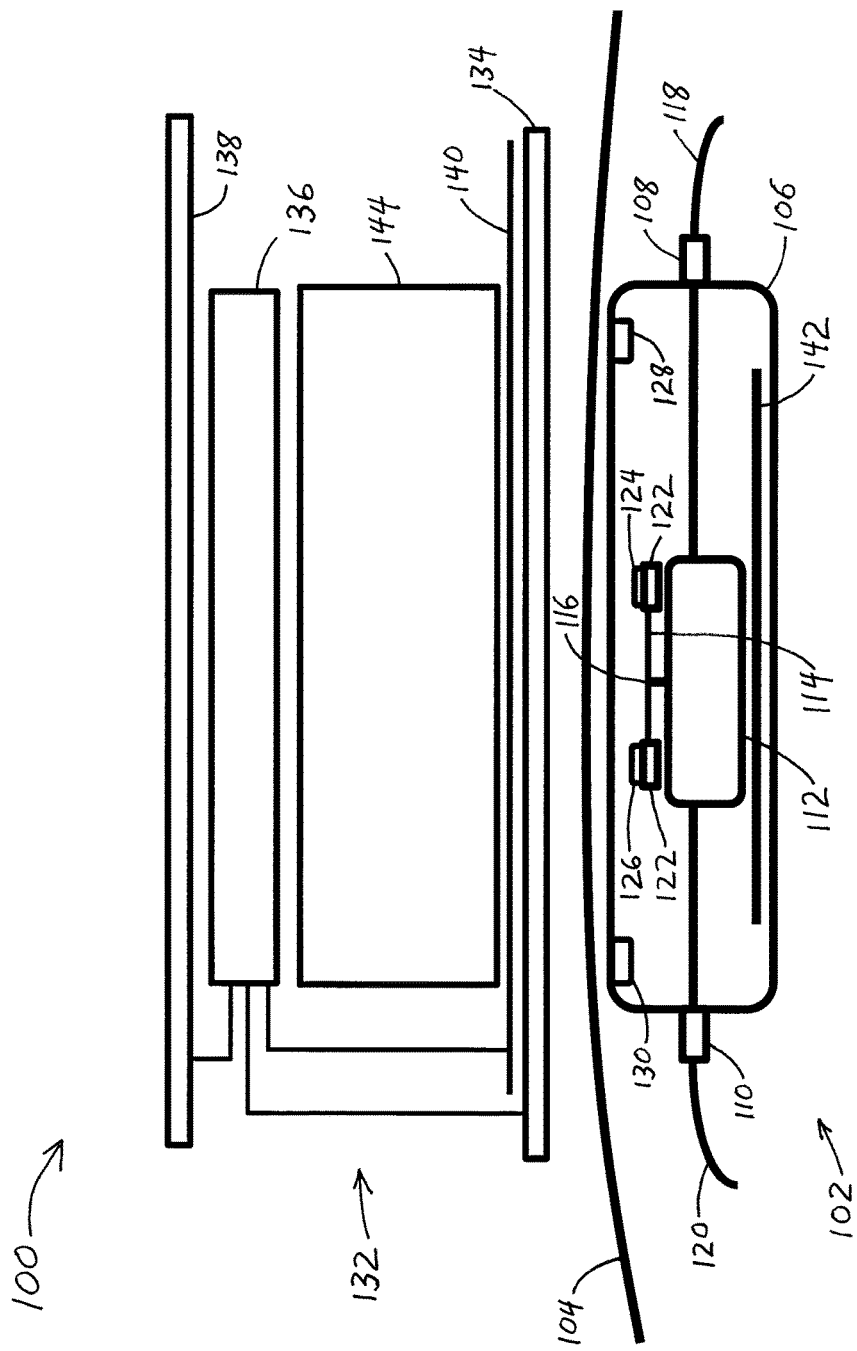
FIG. 1 schematically illustrates in a side cutaway view, an exemplary embodiment of an implantable valve system according to the present invention.

Referring more particularly to the figures, FIG. 1 schematically illustrates in a side cutaway view, an exemplary embodiment of an implantable valve system 100 according to the present invention. The system 100 is seen to comprise an implantable valve 102 illustrated in FIG. 1 as implanted beneath the skin 104 of a patient. The valve 102 comprises a hermetic biocompatible housing 106, a fluid inlet port 108, a fluid outlet port 110, and a restriction element 112 therebetween for restricting fluid transport between the inlet port 108 and the outlet port 110. The valve 102 further comprises a control member 114 operatively coupled to the restriction element 112. In an embodiment, rotation of the control member 114 about an axis 116 serves to adjust a setting of the valve 102. In an embodiment, the valve 102 is a CSF drainage valve used to treat hydrocephalus. In a further embodiment, a first catheter 118 coupled to the inlet port 108 conducts fluid from a ventricle of a brain to the valve 102, and a second catheter 120 coupled to the outlet port 110 directs fluid exiting the valve 102 to a drainage site elsewhere in the body of the patient. Implantable CSF drainage valves having hermetic biocompatible housings, inlet and outlet ports and a restriction element operatively coupled to a rotatable control member are well known in this art, such as, for example, DePuy Synthes' CODMAN® HAKIM® Programmable Valve and the DePuy Synthes' CODMAN CERTAS® Plus Programmable Valve System.

In one embodiment, the restriction element 112 comprises a variable aperture, a cross section of which is adjustable by rotation of the control member 114 about the axis 116. In another embodiment, the restriction element 112 comprises a resiliently sealed aperture through which CSF will flow if the fluid pressure difference across the restriction element 112 exceeds a predetermined minimum. In an embodiment, the control member 114 comprises a plurality of discrete rotational stops corresponding to predetermined quantitative flow or pressure settings of the valve 102. In an embodiment, the control member 114 includes one or more magnets 122, wherein application of a magnetic field from an external source can be used to rotate the control member 114, thereby changing a setting of the valve 102.

The valve 102 is also seen to comprise a plurality of light-emitting elements 124, 126, 128, 130. In an embodiment the plurality of light-emitting elements comprises at least three solid-state light-emitting elements. In one embodiment one or more of the light-emitting elements is a light-emitting diode. In another embodiment one or more of the light-emitting elements is a laser diode. Each of the light-emitting elements is configured to direct light generally out of the body from its respective location at the valve, and each of the light-emitting elements is selected to emit light at a wavelength that is at least partially transmissible through the patient's skin 104 overlying the valve 102.

As illustrated in FIG. 1, two light-emitting elements 124, 126 are seen to be mounted to the control member 114 and spatially separated therealong. One or more additional light emitting elements, illustrated as two light-emitting elements 128, 130 are also seen to be mounted to the valve 102 at a location spatially separated from the control member 114. When the light-emitting elements are energized, some of the emitted light from each light-emitting element reaches the surface of the patient's skin 104, where it can be imaged to provide information regarding the location and setting of the valve 102. Maximizing the spatial separation among the light-emitting elements within the physical limits of the valve housing 106 is generally advantageous for systems according to the present invention, to minimize the effects of optical scattering from passage of the light through the skin 104. In another embodiment, the light-emitting elements of the present invention indicate the location and orientation of the valve, and a different technology is used to provide information regarding the current setting of the valve. In yet another embodiment, the means for providing information regarding the current setting of the valve comprises magnetic sensing.

The selection of an emission wavelength of a light emitter for use in an implantable valve and system according to the present invention is based on the availability of practical solid state light emitters at the wavelength, the availability of solid state imaging arrays, additionally discussed hereinbelow, for detecting light at the wavelength, and optical transmission of human skin at the wavelength, where greater optical transmission is advantageous for systems according to the present invention. In general through the visible and near infrared spectral regions of approximately 400 nm to 1000 nm in which light-emitting diodes and laser diodes are currently commercially available, human skin transmits longer wavelength light more effectively than it does shorter wavelength light. A selection of optimal operating wavelengths for a system according to the present invention is one of engineering tradeoffs, and a selection of any wavelengths having a functional combination of an available light source, an available imaging sensor and effective transmission through human skin, is within the scope of the present invention. In one embodiment, light-emitting elements according to the present invention are selected to emit light in the red and near-infrared spectral regions of approximately 600 nm to 1000 nm.

The system 100 according to the present invention as schematically illustrated in FIG. 1 is also seen to comprise a non-invasive locator and indicator tool 132 for identifying the location of the valve 102 beneath the skin 104, and for reading a setting of the valve 102. The tool 132 is seen to comprise a solid state imaging array 134 such as is commonly used in both still and video imaging. Light emitted by the light-emitting elements and transmitted through the skin 104 to the outside of the body is detected by the imaging array 134. As illustrated in FIG. 1, the imaging array 134 or a protective transparent window mounted thereon is positionable directly on the skin 104 or in proximity thereto above the implanted location of the valve 102. In another embodiment (not illustrated), the skin 104 above the valve 102 is imaged to the imaging array by one or more of an imaging lens or a lenticular array. In yet another embodiment, the skin 104 above the valve 102 is imaged using a scanning optical detection system.

The tool 132 is also seen to functionally comprise an electronics module 136 for processing the detected light to determine the location of the valve 102 beneath the skin 104 and to determine a current setting of the valve 102. The electronics module 136 can be a discrete physical module, or the components thereof can be distributed in any functional manner about the tool 132. A graphic display panel 138 is also seen to be coupled to the electronics module 136. In another embodiment, one or both of the electronics module 136 and the graphic display 138 comprises a wired or wireless interface to a portable electronic device, such as a smartphone.

Electrical power is required for operation of the light emitters in the valve 102, and any means for wirelessly transmitting electrical power to the valve 102 can be used in systems according to the present invention. In one embodiment, the tool 132 further comprises a power transmitting antenna 140 for wirelessly transmitting electrical power to the valve 102, the valve 102 comprising a corresponding one or more receiving antenna 142 for receiving the power signal from external antenna 140 to provide electrical power to the implantable light-emitting elements. In another embodiment, electrical power for operating the light-emitting elements is transmitted optically to the valve 102. Optical transmission of electrical power to a surgical implant is known in this art, as disclosed, for example, in U.S. Pat. No. 7,844,342 to Dlugos, Jr. et al., which is hereby incorporated by reference in its entirety.

The locator and indicator tool 132 can also incorporate functionality to adjust a setting of the valve 102. In an embodiment, the valve 102 is a magnetically adjustable valve and the tool 132 further includes a valve adjustment section 144 comprising one or more magnet or electromagnet for magnetically coupling to the control member 114 for adjusting the valve 102. Whereas compass-type reading of a magnetically adjustable valve generally is incompatible with the presence of a powerful magnet required to adjust the valve, optical reading of a valve according to the present invention can be performed in the presence of a strong magnetic field, thereby enabling simultaneous reading and adjustment of a magnetically adjustable valve.

Figure 2:
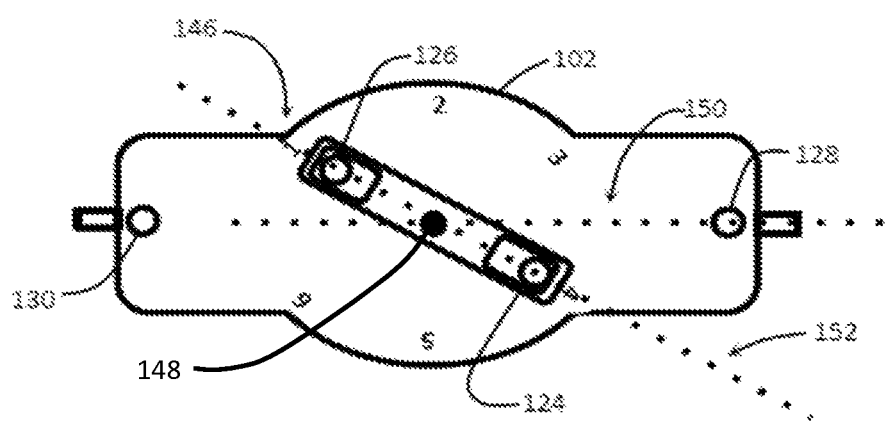
FIG. 2 schematically illustrates in a top cutaway view, an implantable valve according to the present invention, showing light-emitting elements associated with the valve.

Now turning to FIG. 2, an embodiment of the valve 102 of FIG. 1 is shown schematically in a top cutaway view illustrating exemplary relative locations of light-emitting elements 124, 126, 128, 130 associated with the valve 102. Valve 102 has, for example, six pressure settings as indicated by numerals 1-6 in FIG. 2. Light-emitting element 126 can, for example, align with the setting of the valve. Thus, the valve illustrated in FIG. 2 is set at pressure setting 1, as illustrated by rotational setting 146. The light-emitting elements are arrayed substantially in a single plane. To read the setting of the valve 102, measurement of the relative positions of the two light emitters 124, 126 associated with the control member 114 and at least one other light emitter 128 is required. That is, at least three light emitters are required to determine the location, orientation and setting of the valve 102.

In an exemplary embodiment, a geometrical mid-point between the two light emitters 124, 126 associated with the control member 114 provides a center reference 148 for locating the valve 102. A geometrically determined line between the center reference 148 and one of the other illustrated light emitters 128 provides an orientational reference axis 150 with respect to the valve 102, and the angle between the reference axis 150, and a line 152 geometrically determined between the two light emitters 124, 126 associated with the control member 114 provides the valve setting. Optionally one or more additional light emitter 130 can be used to enhance the determination of the orientation and setting of the valve 120.

In addition to providing analysis of geometrical relationships among the locations of the at least three light emitters, the light-emitting properties of the various light emitters can be made distinct from one another to enhance the ability of the imaging to resolve their individual positions. In one embodiment, each of the at least three light emitters is pulsed at a unique pulsing frequency and the image data is processed to distinguish among these three distinct signals to improve signal quality. In another embodiment the at least three light emitters are each configured to emit light at a different wavelength than the other two, and the imaging array 134 comprises a color imager that distinguishes among the three distinct wavelengths to improve signal quality. In addition, the unique identification of each light emitter can provide verification of the absolute location of each light emitter with respect to the valve 102.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A valve for implantation beneath the skin of a patient, the valve comprising:
   a fluid inlet port;
   a fluid outlet port;
   a restriction element therebetween for restricting fluid transport between the inlet port and the outlet port;
   a control member operatively coupled to the restriction element for setting at least one of a rate of fluid flow through the restriction element and a pressure drop across the restriction element, a physical orientation of the control member being indicative of the setting; and
   at least two light-emitting elements coupled to the control member and physically spaced apart from one another along a length of the control member;
   wherein light emitted by the at least one light-emitting element is externally detectable through the skin of the patient for reading the setting.

2. The valve according to claim 1 wherein the two light-emitting members differ from one another by at least one of a difference in wavelengths of the respective light emission and a difference in a time dependence of the intensity of the respective light emission.

3. The valve according to claim 1 wherein at least one of the light-emitting elements is a light-emitting diode.

4. The valve according to claim 1 wherein at least one of the light-emitting element comprises emission wavelengths in one or more of the visible and near infrared spectral regions.

5. The valve according to claim 1 wherein the light emitted by at least one of the light-emitting elements is pulsed.

6. The valve according to claim 1, further comprising a housing that is transmissive of light emitted by at least one of the light-emitting elements, the control member being disposed in the housing.

7. A valve for implantation beneath the skin of a patient, the valve comprising:
   a fluid inlet port;
   a fluid outlet port;

a restriction element therebetween for restricting fluid transport between the inlet port and the outlet port;
a control member operatively coupled to the restriction element for setting at least one of a rate of fluid flow through the restriction element and a pressure drop across the restriction element, a physical orientation of the control member being indicative of the setting; and
a first light-emitting element coupled to the control member; and
a second light-emitting element coupled to the control member;
wherein light emitted by at least the first light-emitting element is externally detectable through the skin of the patient for reading the setting, and
wherein light emitted by the second light-emitting element is externally detectable through the skin of the patient and indicative of at least one of a location and a physical orientation of the valve under the skin of the patient.

8. The valve according to claim 7, wherein the second light-emitting element comprises emission wavelengths in one or more of the visible and near infrared spectral regions.

9. The valve according to claim 7, wherein light emitted by the second light-emitting element and light emitted by the first light-emitting element are distinguishable from one another by at least one of a difference in wavelengths of the respective light emission and a difference in a time dependence of the intensity of the respective light emission.

10. The valve according to claim 7, further comprising an antenna electrically connected to the first light-emitting element receiving an externally generated electromagnetic signal and for providing electrical power to the second light-emitting element.

11. The valve according to claim 7 further comprising at least a third additional light-emitting element coupled to the housing but spaced from the control member, wherein light emitted by the at least a third additional light-emitting element is externally detectable through the skin of the patient and indicative of at least one of a location and a physical orientation of the valve under the skin of the patient.

12. A valve for implantation beneath the skin of a patient, the valve comprising:
a fluid inlet port;
a fluid outlet port;
a restriction element therebetween for restricting fluid transport between the inlet port and the outlet port;
a control member operatively coupled to the restriction element for setting at least one of a rate of fluid flow through the restriction element and a pressure drop across the restriction element, a physical orientation of the control member being indicative of the setting;
at least one light-emitting element coupled to the control member; and
an antenna electrically connected to the at least one light-emitting element receiving an externally generated electromagnetic signal and for providing electrical power to the at least one light-emitting element,
wherein light emitted by the at least one light-emitting element is externally detectable through the skin of the patient for reading the setting.

13. A method for non-invasively reading a setting of an adjustable valve implanted beneath the skin of a patient, the method comprising:
detecting through the skin, light emitted by at least three physically distributed light sources within the valve;
mapping the relative locations of the at least three light sources, and
calculating a current setting of the valve from the mapped locations.

14. The method according to claim 13 wherein at least two of the light sources differ from one another with respect to at least one of an emitted wavelength of light and a time dependence of the light emission.

15. The method according to claim 13 further comprising the step of: adjusting the valve with a magnet while simultaneously reading the setting of the valve.

16. A system for reading a setting of an adjustable fluid flow valve implanted beneath the skin of a patient, the valve comprising at least three light emitters, the relative locations of the light emitters being indicative of the setting, the system comprising:
an electronic imaging array for imaging light emitted by the at least three light emitters and transmitted through the skin; and
an electronic processor for determining the setting of the valve from the image; and
a display for indicating the setting of the valve.

17. The system according to claim 16 wherein the imaging array is positionable one of on and closely above the surface of the skin under which the valve is implanted.

18. The system according to claim 16 wherein the display further indicates at least one of a location and a spatial orientation of the implanted valve.

19. The system according to claim 16 further comprising an energy transmitting antenna for transmitting electrical power to the light emitters.

20. The system according to claim 16 wherein the valve is a magnetically adjustable valve; and further comprising a magnetic adjustment component for adjusting a setting of the valve.

21. The system according to claim 17 wherein the electronic imaging array comprises a planar array of imaging pixels; and the magnetic adjustment component is operable with the imaging array positioned between the magnetic adjustment component and the skin above the valve location.

22. A system comprising a valve for implantation beneath the skin of a patient and an external control unit for reading a setting of the valve implanted beneath the skin of a patient, the system comprising a valve comprising:
a fluid inlet port;
a fluid outlet port;
a restriction element therebetween for restricting fluid transport between the inlet port and the outlet port;
a control member operatively coupled to the restriction element for setting at least one of a rate of fluid flow through the restriction element and a pressure drop across the restriction element, a physical orientation of the control member being indicative of the setting; and
at least three light emitters, the relative locations of the light emitters being indicative of the setting of the valve;
the external control unit comprising:
an electronic imaging array for imaging light emitted by the at least three light emitters and transmitted through the skin; and
an electronic processor for determining the setting of the valve from the image; and a display for indicating the setting of the valve.

* * * * *